US00PP15763P3

(12) United States Plant Patent
Noack

(10) Patent No.: US PP15,763 P3
(45) Date of Patent: May 17, 2005

(54) SHRUB ROSE PLANT NAMED 'ANGELSIE'

(50) Latin Name: *Rosa hybrida*
Varietal Denomination: Angelsie

(75) Inventor: Reinhard Noack, Gütersloh (DE)

(73) Assignee: Angelica Nurseries, Inc., Kennedyville, MD (US)

( * ) Notice: Subject to any disclaimer, the term of this patent is extended or adjusted under 35 U.S.C. 154(b) by 87 days.

(21) Appl. No.: 10/075,873

(22) Filed: Feb. 13, 2002

(65) Prior Publication Data

US 2003/0154526 P1 Aug. 14, 2003

(51) Int. Cl.[7] ..... A01H 5/00

(52) U.S. Cl. ..... Plt./102

(58) Field of Search ..... Plt./102, 107, 108, Plt./106, 141, 142, 143, 148, 149

*Primary Examiner*—Howard J. Locker
(74) *Attorney, Agent, or Firm*—RatnerPrestia

(57) ABSTRACT

A new and distinct rose variety of the shrub class which is particularly well suited for growing as an attractive ornamentation to the landscape, characterized by its continuous and abundant production of long-lasting brilliant orange-pink flowers, its upright, dense and bushy growth habit, its attractive glossy foliage that contrasts well with the brilliant orange-pink blooms, and its outstanding disease resistance.

1 Drawing Sheet

Genus and Species: *Rosa hybrida*
Varietal Denomination: 'Angelsie'.

FIELD OF THE INVENTION

This invention relates to a new and distinct variety of rose plant of the shrub rose class.

SUMMARY OF THE INVENTION

The present invention relates to a new and distinct variety of rose plant of the shrub class, which is particularly well suited for growing as an attractive ornamentation to the landscape. The varietal denomination of this new and distinct variety of rose plant is 'Angelsie', and the commercial name is 'Lady Elsie May.'

By cross pollination of the variety known as 'Repandia' (an unpatented light pink shrub rose, W. Kordes' Söhne, 1982) with the variety known as 'Gruss an Angeln' (an unpatented medium red hybrid tea rose, Noack Rosen, 1986), I have produced a new and improved rose variety which is distinguished from all other rose varieties of which I am aware, as evidenced by the following unique combination of characteristics which are outstanding therein:

(1) Its continuous and abundant production of long-lasting brilliant orange-pink flowers.

(2) Its upright, dense and bushy growth habit.

(3) Its attractive glossy foliage that contrasts well with the brilliant orange-pink blooms.

(4) Its outstanding disease resistance.

Asexual reproduction of this new variety by budding was first performed in Gütersloh, Germany. Asexual reproduction of this new variety by rooted cuttings in Kent County, on the eastern shore of Maryland, shows that the foregoing and all other characteristics come true to form and are established and transmitted through succeeding propagations.

BRIEF DESCRIPTION OF THE ILLUSTRATION

The accompanying illustration shows typical specimens of the vegetative growth and flower of this new variety in different stages of development, depicted in color as nearly true as it is reasonably possible to make the same in a color illustration of this character.

DETAILED DESCRIPTION OF THE NEW VARIETY

The following is a detailed description of my new rose cultivar with color descriptions using terminology in accordance with a Royal Horticulture Society Colour Chart (R.H.S.C.C.), except where ordinary dictionary significance of color is indicated.

Parentage: 'Repandia' (unpatented)×'Gruss an Angeln' (unpatented).
Class: Shrub.

The following observations are made of one-year old specimens grown outdoors in Kent County, Md., during the month of September.

FLOWER

Blooming habit: Recurring, continuous.

A. Bud:

*Size.*—Small. About ½ to ¾ inch long when the petals start to unfurl.

*Form.*—Long and pointed.

*Sepals.*—Curling back as the bud opens. Length — about ¾ inch to 1 inch. There are three normally appendaged sepals. There are two unappendaged sepals. Shape — triangular, pointed with slight serration at tip. Texture — slightly hairy. Color: Upper side — Green Group 139B. Underside — Greyed Green Group 193D.

*Color.*—Red Group 53B when sepals start to unfurl.

*Peduncle.*—Length — 1 to 1½ inch long. Straight, erect. Surface — Smooth, prickly. Color — Green Group 138A, sometimes aging to Greyed Red Group 182A.

*Calyx tube.*—Length — about ¼ inch long. Aspect — smooth. Color — Green Group 141C.

B. Bloom:

*Size.*—Average open size is about 3 inches.

*Borne.*—In sprays containing 6 to 12 blooms and in clusters containing up to three sprays.

*Stems.*—Short, typically about 3 to 6 inches.

*Form.*—Initially cup-shaped, flattening on maturity.

*Fragrance.*—Rose fragrance.

C. Petals:

*Size.*—Length: typically about 1½ inches. Width: typically about 1½ inches.

*Shape.*—Triangular. Margins entire with a slight indentation near the center of the outer margin.

*Texture.*—Smooth.

*Arrangement.*—Symmetrically arranged in a circular outline.

*Number.*—Under normal conditions typically about 10–11, with 1 to 3 petaloids in the center.

*Color.*—American Rose Society color classification: Orange-pink. When first opened, the upper side is close to Red Group 46C. The under side is close to Red Group 52B.

*Color change.*—As the bloom ages the edge of the upper side of the petals tends to Red Purple Group 66A and the petals typically become mottled. The underside tends to Red Purple Group 57C.

*Persistence.*—Drop off cleanly.

*Lasting quality.*—On the plant: Long, at least 10–12 days.

REPRODUCTIVE PARTS

A. Reproductive parts:

*Stamens.*—Length — about ½ inch.

*Anthers.*—Size: Medium, about ⅛ inch. Quantity: Many, about 80. Color: Yellow-Orange, near Yellow-Orange Group 22-A. Arrangement: Regular around styles.

*Filaments.*—Color: Red near Red Group 39A.

*Pollen.*—Color: Greyed Orange Group 163A.

*Styles, stigmas, and pistils.*—None observed. Instead of styles, stigmas, and pistils, the flower contains a continuous disc, Yellow Green Group 151C.

B. Hips: None observed.

C. Seeds: None observed.

PLANT

A. Form: Upright.

B. Growth: Very vigorous, uniform branching on main stems, new growth occurs regularly throughout season. Height obtained in first season — about 1½ to 2 feet. Mature Plant: Height — about 3 feet. Width — about 3 ft.

C. Foliage: Compounded; 5 to 7 leaflets on normal mid-stem leaves, typically 5 leaflets on leaves on main canes.

*Size.*—Leaflets — ¾ to 1½ inches long and ½ to 1 inch wide.

*Quantity.*—Abundant, covers plant to ground.

*Arrangement.*—Alternate; Uniform and equally spaced.

*Color.*—New foliage: Upper side — near to Green Group 137A; under side — near Green Group 137C. Old foliage: upper side — Green Group 139A, under side — Yellow Green Group 147B.

*Shape.*—Oval with slight point at tip.

*Venation.*—Non-parallel.

*Texture.*—Upper side — leathery, glossy. Under side — smooth between ribs.

*Edge.*—Serrated.

*Serration.*—Very small and uniform.

*Petiole.*—Color: Upper side — Green Group 138A. Under side — Yellow-Green Group 146D. Texture — Smooth. Length — ¾ to 1¾ inches.

*Rachis.*—Color — Yellow-Green Group 144B. Texture — Smooth.

*Stipules.*—Shape — Pointed. Texture — Medium smooth. Color: Yellow-Green Group — 146A. Length — about ½ inch. Width at top. — about ¼ inch.

*Resistance to disease.*—Blackspot — Outstanding. Mildew Outstanding. Rust — none observed in three-year field tests.

D. Wood:

*New wood.*—Color — Greyed-Orange Group 177A. Bark — smooth.

*Old wood.*—Color — Green Group 138A. Bark — smooth.

E. Thorns and prickles:

*Prickles.*—Quantity — ordinary. Shape — pointed and curved down. Form — flat base. Length — about ⅛ to ¼ inch. Color (when young) — Green-White Group — 157A. Color (when mature) — Greyed Orange Group 176B. Position — irregular.

F. Winter hardiness: Excellent. Hardy to zone 4.

I claim:

1. A new and distinct variety of rose plant of the shrub class which is particularly well suited for growing as an attractive ornamentation to the landscape, substantially as herein shown and described, characterized particularly as to novelty by its continuous and abundant production of long-lasting brilliant orange-pink flowers, its upright, dense and bushy growth habit, its attractive glossy foliage that contrasts well with the brilliant orange-pink blooms, and its outstanding disease resistance.

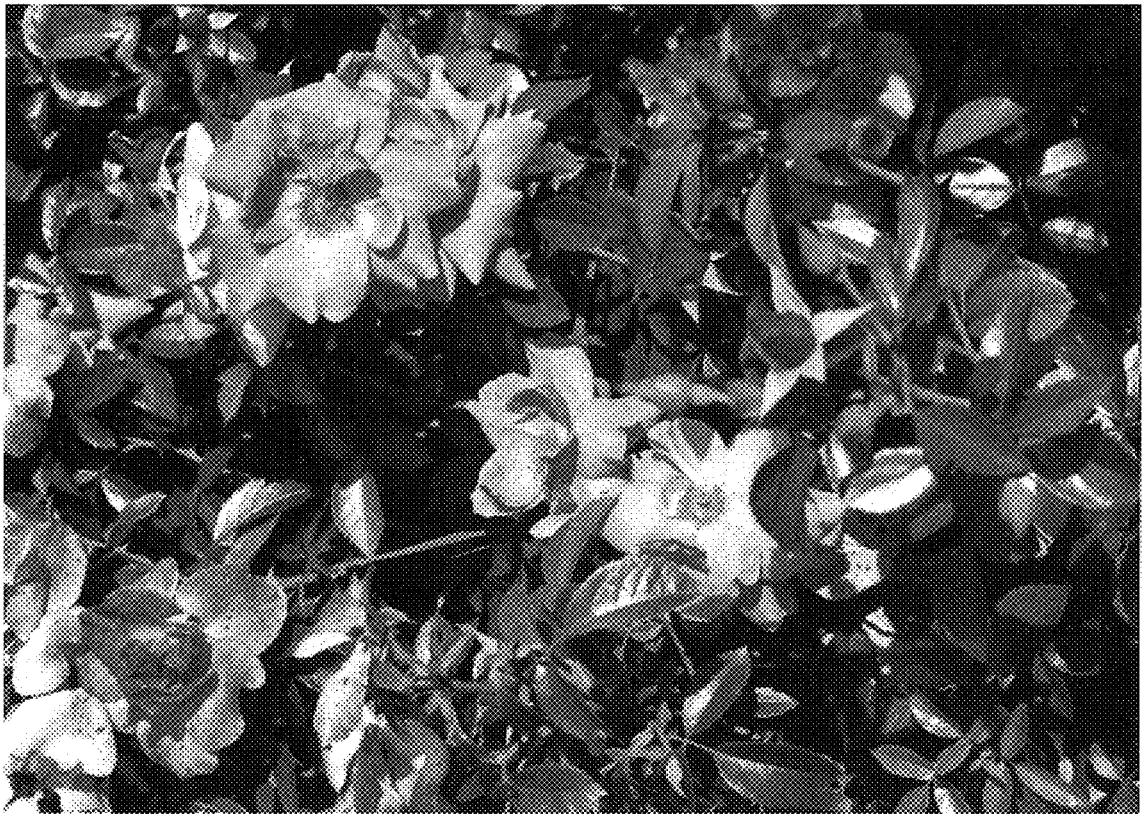

* * * * *